United States Patent [19]

Hanson et al.

[11] Patent Number: 5,416,092
[45] Date of Patent: May 16, 1995

[54] 3-AZABICYCLO[3.2.1]-OCT-8-YL-TERMINATED NON-PEPTIDYL α-SUCCINAMIDOACYL AMINODIOLS AS ANTI-HYPERTENSIVE AGENTS

[75] Inventors: Gunnar J. Hanson, Skokie; John S. Baran, Winnetka, both of Ill.

[73] Assignee: G. D. Searle & Co., Chicago, Ill.

[21] Appl. No.: 186,731

[22] Filed: Jan. 25, 1994

Related U.S. Application Data

[60] Division of Ser. No. 732,880, Jul. 19, 1991, which is a continuation of Ser. No. 103,623, Oct. 1, 1987, abandoned.

[51] Int. Cl.$^6$ .................. A61K 31/46; C07D 451/02
[52] U.S. Cl. .................. 514/304; 546/127; 546/129; 546/130; 546/131; 546/132
[58] Field of Search .................. 514/19, 304; 546/132

[56] References Cited

FOREIGN PATENT DOCUMENTS

| | | |
|---|---|---|
| 0128762 | 12/1984 | European Pat. Off. . |
| 0172346 | 2/1986 | European Pat. Off. . |
| 0172347 | 2/1986 | European Pat. Off. . |
| 0181110 | 5/1986 | European Pat. Off. . |
| 0189203 | 7/1986 | European Pat. Off. . |
| 0200406 | 12/1986 | European Pat. Off. . |

OTHER PUBLICATIONS

H. Umezawa, et al, *The Journal of Antibiotics* (Tokyo) 23, pp. 259–262, (1970).
F. Gross, et al, *Science*, 175, p. 656, (1971).
J. Boger, et al, *Nature*, 303, pp. 81–84, (1983).
T. Kokubu, et al, *Biochem. Biophys. Research Commun.*, 118, pp. 929–933, (1984).
Fehrentz, et al, *FEBS Lett.*, 167, pp. 273–276, (1984).
G. Hanson, et al, *Biochem. Biophys. Research Commun.*, 132, pp. 155–161, (1987).
G. Hanson, et al, *Biochem. Biophys. Research Commun.*, 146, pp. 959–963, (1987).
G. Marshall, *Federation Proceedings*, 35, pp. 2494–2501, (1976).
J. Burton, et al, *Proc. Natl. Acad. Sci. USA*, 77, pp. 5476–5479, (1980).
Y. Suketa, et al, *Biochemistry*, 14, pp. 3188–3194, (1975).
J. Swales, *Pharma. Ther.*, 7, pp. 173–201, (1979).
Kokubu, et al, *Nature*, 217, pp. 456–457, (1968).
Y. Matsushita, et al, *The Journal of Antibiotics*, 28, pp. 1016–1018, (1975).
J. Lazar, et al, *Biochem. Pharma.*, 23, pp. 2776–2778, (1974).
R. Miller, et al, *Biochem. Pharma.*, 21, pp. 2941–2944, (1972).
E. Haber, *Clinical Science*, 59, pp. 7s–19s, (1980).
D. Rich, et al, *J. Org. Chem.*, 43, pp. 3624–3626, (1978).
D. Rich, et al, *J. Med. Chem.*, 23, pp. 27–33, (1980).
E. Haber, *Clin. and Exper. Hyper.*, A5(7&8), pp. 1193–1205, (1983).

*Primary Examiner*—Joseph Paul Brust
*Attorney, Agent, or Firm*—J. Timothy Keane

[57] ABSTRACT

Non-peptidyl compounds characterized generally as α-succinamidoacyl aminodiols having a 3-azabicyclo[3.2.1]-oct-8-yl-type group at the N-terminus are useful as renin inhibitors for the treatment of hypertension.

10 Claims, No Drawings

3-AZABICYCLO[3.2.1]-OCT-8-YL-TERMINATED NON-PEPTIDYL α-SUCCINAMIDOACYL AMINODIOLS AS ANTI-HYPERTENSIVE AGENTS

RELATED APPLICATION

This is a divisional of U.S. Application Ser. No. 07/732,880 filed Jul. 19, 1991, which is a continuation of Ser. No. 07/103,623 filed Oct. 1, 1987, now abandoned.

FIELD OF THE INVENTION

Renin-inhibiting compounds are known for control of hypertension. Of particular interest herein are non-peptidyl compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23:259–262 (1970)]. This peptide, known as pepstatin, was found to reduce blood pressure in vivo after the the injection of hog renin into nephrectomized rats [Gross et al, *Science*, 172, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger, et al, *Nature*, 303, 81 (1983)]; high molecular weight peptides are generally considered undesirable as drugs because gastrointestinal absorption is impaired and plasma stability is compromised.

Short peptide aldehydes have been reported as renin inhibitors [Kokubu et al, *Biochem. Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glycol-containing compounds as renin inhibitors [also see Hanson et al, *Biochem. Biophys. Res. Comm.*, 132:155-161 (1985), 146:959-963 (1987)]. EP Appl. #181,110, published May 14, 1986, describes dipeptide histidine derivatives as renin inhibitors. EP Appl. #189,203, published Jul. 30, 1986, describes peptidylaminodiols as renin inhibitors. EP Appl. #200,406, published Dec. 10, 1986, describes alkyl naphthylmethyl propionyl-histidyl aminohydroxy alkanoates as renin inhibitors.

For other articles describing previous efforts to devise renin inhibitors, see Marshall, *Federation Proc.*, 35: 2494–2501 (1976); Burton et al, *Proc. Natl. Acad. Sci. USA*, 77: 5476–5479 (1980); Suketa et al, *Biochemistry*, 14: 3188 (1975;) Swales, *Pharmac. Ther.*, 7: 173–201 (1979); Kokubu et al, *Nature*, 217: 456–457 (1986); Matsushita et al, *J. Antibiotics*, 28: 1016–1018 (1975); Lazar et al, *Biochem. Pharma.*, 23:2776–2778 (1974); Miller et al., *Biochem. Pharma.*, 21:2941–2944 (1972); Haber, *Clinical Science*, 59: 7s–19s (1980); Rich et al, *J. Org. Chem.*, 45: 3624 (1978); *J. Med. Chem.*, 23: 27 (1980); especially Haber, *Clin. and Exper. Hyper.*, A5(7&8), 1193 (1983); and European Patent Applications 172346A and 172347A published Feb. 26, 1986.

DESCRIPTION OF THE INVENTION

Non-peptidyl α-succinamidoacyl aminodiols compounds having utility as renin inhibitors for treatment of hypertension in mammals constitute a family of compounds of general Formula I:

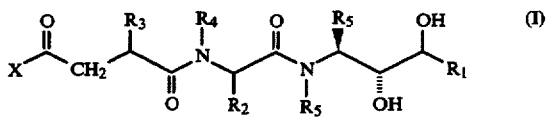

wherein X is selected from

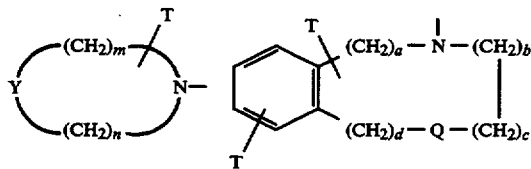

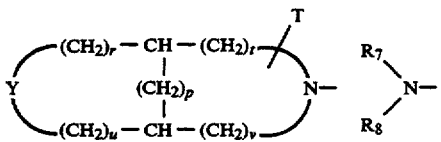

wherein Y and Q are selected from CH$_2$,

O, S, SO, SO$_2$ and NR$_{10}$, wherein R$_9$ is H or lower alkyl, R$_{10}$ is selected from H, phenyl and

and wherein R$_{11}$ is H or lower alkyl; wherein each of m and n is independently an integer from 1 through 4; wherein each of r, t, u and v is independently an integer from zero through two; wherein p is an integer from 1 through 3; wherein each of a through d is independently an integer from zero through 3; wherein T is selected from one or more groups selected from H, linear or branched lower alkyl, alkoxy, oxo, halo, haloalkyl, lower alkenyl, lower alkynyl and cyano; wherein R$_1$ is selected from H, linear or branched lower alkyl, haloalkyl, alkylcycloalkyl, alkylcycloalkenyl and alkoxycarbonyl; wherein $R_2$ is selected from linear or branched lower alkyl and benzyl; wherein $R_3$ is selected from lower alkyl, acylaminoalkyl, benzyl, naphthylmethyl, aryl and benzyl substituted at the phenyl portion by halo or lower alkyl or by both; wherein each of $R_4$ and $R_5$ is independently selected from H or lower alkyl; wherein $R_6$ is selected from substituted or unsubstituted cycloalkyl, phenyl, cycloalkylalkyl and phenylalkyl, any one of which may be substituted with one or more groups selected from alkyl, alkoxy, halo, haloalkyl, lower alkenyl, lower alkynyl and cyano; and wherein each of $R_7$ and $R_8$ is independently selected from the groups H, lower alkyl, cycloalkyl, phenyl, benzyl, naphthyl and naphthylmethyl, any one of which groups having a substitutable position may be optionally substituted with or more of lower alkyl, alkoxy, alkenyl, alkynyl, halo, haloalkyl, cyano and phenyl, with the proviso that at least one of $R_7$ and $R_8$ is an aryl group.

A preferred group of compounds within Formula I are hose compounds having the specific stereochemical configuration shown in Formula II:

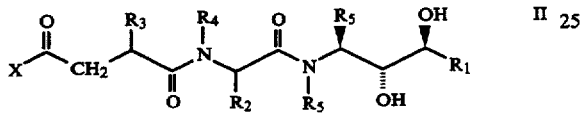

II

Preferred compounds within Formula II are those compounds of Formula ! wherein Y and Q are selected from O, $CH_2$, S, $NR_{10}$ wherein $R_{10}$ is H or

wherein $R_{11}$ is H or lower alkyl; wherein each of m and n is independently an integer from 1 through 3; wherein each of r, t, u and v is independently zero or one; wherein p is one or two; wherein each of a through d is independently an integer from zero through 2; wherein T is selected from one or more groups selected from H, lower alkyl, alkoxy, oxo and halo; wherein $R_1$ is selected from H, lower alkyl, alkylcycloalkyl and alkoxycarbonyl; wherein $R_2$ is selected from lower alkyl and benzyl; wherein $R_3$ is selected from lower alkyl, acylaminoalkyl, benzyl, napthylmethyl, aryl and benzyl substituted at the phenyl portion by halo or lower alkyl or by both; wherein $R_4$ is selected from H and lower alkyl; wherein $R_5$ is H lower alkyl; wherein $R_6$ is selected from cyclohexylmethyl and benzyl; wherein each of $R_7$ and $R_8$ is independently selected from H, phenyl, naphthyl and phenyl substituted with one or more lower alkyl, alkoxy, alkenyl, halo, cyano and phenyl, with the proviso least one of $R_7$ and $R_8$ is phenyl.

Within the aforementioned preferred group of compounds, there are four sub-groups of preferred compounds. The first sub-group consists of those compounds of Formula II wherein X is

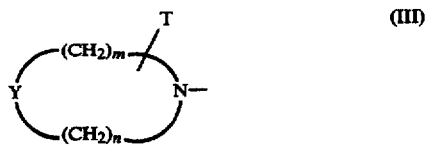

(III)

wherein Y is O, $CH_2$, or S; m is 2; n is 2; T is one or more of H or lower alkyl; $R_1$ is H or methyl; or lower alkyl; $R_2$ is lower alkyl; $R_3$ is benzyl; $R_4$ is H; $R_5$ is H; and $R_6$ is cyclohexylmethyl. Of this first sub-group the most preferred are those compounds wherein Y is O, m is 2; n is 2; T is one or more of H or methyl; $R_1$ is selected from H, methyl, ethyl and isobutyl; $R_2$ is isobutyl; $R_3$ is selected from benzyl and napthylmethyl; $R_4$ is H or methyl; $R_5$ is H or methyl; and $R_6$ is cyclohexylmethyl. Radicals which exemplify the X substituent of Formula III are as follows:

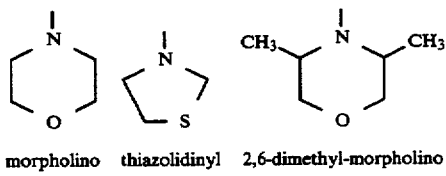

morpholino  thiazolidinyl  2,6-dimethyl-morpholino

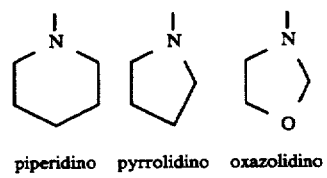

piperidino  pyrrolidino  oxazolidino

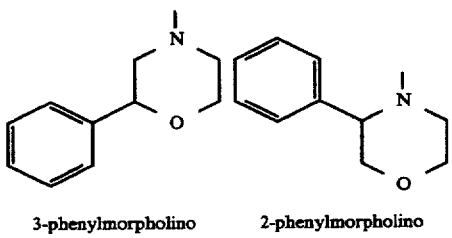

3-phenylmorpholino  2-phenylmorpholino

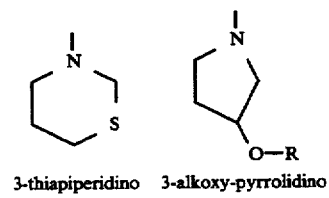

3-thiapiperidino  3-alkoxy-pyrrolidino

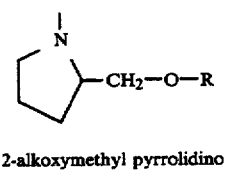

2-alkoxymethyl pyrrolidino

A second sub-group of preferred compounds consists of those within Formula i wherein X is

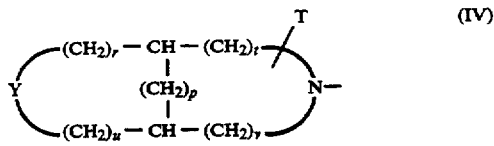

(IV)

wherein Y is selected from O, S, $CH_2$, SO and $SO_2$; wherein each of r, t, u and v is independently zero or one; p is 1 or 2; T is one or more of H, lower alkyl and alkoxy; $R_1$ is lower alkyl; $R_2$ is lower alkyl; $R_3$ is benzyl;

$R_4$ is H or methyl; $R_5$ is H or methyl; and $R_6$ is cyclohexylmethyl. The substituent of Formula IV may be substituted at any substitutable position within the bicyclic structure of Formula IV. Radicals which exemplify the X substituent of Formula IV are as follows:

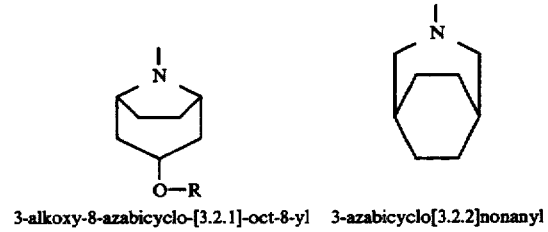

3-alkoxy-8-azabicyclo-[3.2.1]-oct-8-yl    3-azabicyclo[3.2.2]nonanyl

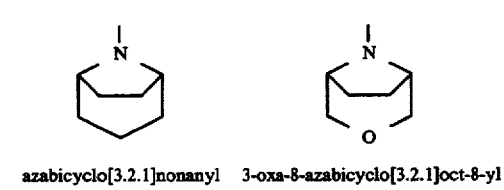

azabicyclo[3.2.1]nonanyl    3-oxa-8-azabicyclo[3.2.1]oct-8-yl

A third sub-group of preferred compounds consists of those compounds wherein X is

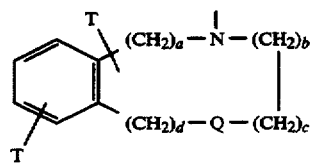

(V)

wherein Q is O, $CH_2$, or S; a is zero; b is 1; c is 1; d is zero; each T is independently one or more of H or lower alkyl; $R_1$ is H or lower alkyl; $R_2$ is lower alkyl; $R_3$ is benzyl; $R_4$ is H or methyl; $R_5$ is H or methyl; and $R_6$ is cyclohexylmethyl.

Within this third sub-group is a set of more preferred compounds of Formula II wherein Q is O, $R_1$ is selected from H, methyl, ethyl and isobutyl, and $R_2$ is isobutyl. Especially preffered is a compound wherein $R_1$ is isobutyl and $R_6$ is cyclohexylmethyl. Another set of more preferred compounds within this third sub-group are those wherein Q is S, $R_1$ is selected from H, methyl and isobutyl, and $R_2$ is isobutyl. Especially preferred is a compound wherein $R_1$ is isobutyl and $R_6$ is cyclohexylmethyl. Radicals which exemplify the X substituent of Formula V are as follows:

benzo-4-thiomorpholino    benzomorpholino

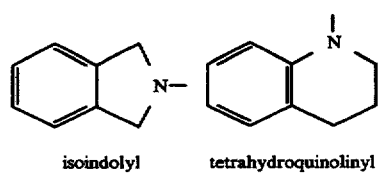

isoindolyl    tetrahydroquinolinyl

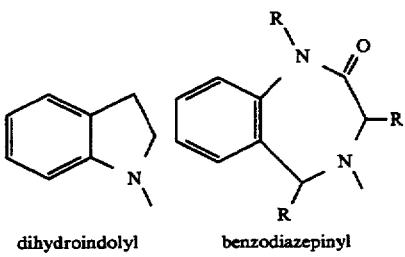

dihydroindolyl    benzodiazepinyl

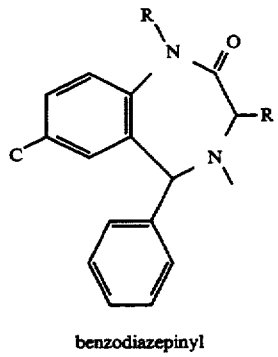

benzodiazepinyl

Within any of these radicals exemplifying Formulae III, IV and V, the substituent R represents a linear or branched alkyl group of one to about ten carbon atoms, or preferably, one to about five caron atoms.

A fourth sub-group of preferred compounds consists of those compounds of Formula II wherein X is

(VI)

wherein each of $R_7$ and $R_8$ is independently selected from the groups H, lower alkyl, cycloalkyl, phenyl, benzyl, naphthyl, and naphthylmethyl, any one of which groups having a substitutable position may be optionally substituted with or more of lower alkyl, alkoxy, alkenyl, alkynyl, halo, haloalkyl, cyano and phenyl, with the proviso that at least one of $R_7$ and $R_8$ is an aryl group.

Of this fourth subgroup, more preferred compounds are those wherein $R_1$ is isobutyl, $R_2$ is isobutyl, $R_3$ is benzyl, $R_4$ is H or methyl, $R_5$ is H or methyl $R_6$ is cyclohexymethyl, and each of $R_7$ and $R_8$ is independently selected from, H, lower alkyl and phenyl, with at least one of $R_7$ and $R_8$ being phenyl. An especially preferred compound is wherein $R_7$ is H and $R_8$ is phenyl.

Unless otherwise described, the chemical groups recited herein shall have meanings as follows: "Lower alkyl" means alkyl radicals containing one to about 10 carbon atoms in a linear or branched configuration, examples of which include methyl, ethyl, n-propyl, isopropyl, n-butyl, sec-butyl, iso-butyl, tert-butyl, n-pentyl, neopentyl, n-hexyl, 1-methylhexyl, n-heptyl, 2-ethylheptyl, n-octyl, 3-propyloctyl, n-nonyl, 4-butylnonyl, n-decyl and the like. "Lower alkenyl" and "lower alkynyl" mean, respectively, hydrocarbon radicals of two to about ten carbon atoms containing at least one carbon-carbon double bond and at least one carbon-carbon triple bond, respectively, attached to alkyl radicals of the type embraced by the term "lower alkyl"

examples of which are 2-butenyl and 3-pentenyl. "Haloalkyl" means alkyl radicals substituted at one or more substitutable positions with one or more halo groups. Preferred haloalkyl group are those provided by lower alkyl radicals substituted an least at one position with one, two or three halo groups such as fluoro or chloro, a specific example of which is trifluoromethyl. "Alkylcycloalkyl" means a cyclized alkyl having from four to about nine ring carbon atoms, any one or more of the substitutable ring carbons being substituted with an alkyl group, preferably a lower alkyl group. "Alkylcycloalkenyl" means a cyclized hydrocarbon radical containing four to about nine ring carbon atoms containing at least one carbon-carbon double bond, but less than the number of double bonds required to form a fully unsaturated ring system, any one or more of the substitutable ring carbon atoms being substituted with an alkyl group, preferably a lower alkyl group. "Alkoxycarbonyl" means an oxycarbonyl radical having an alkyl, preferably lower alkyl, group attached to the oxygen atom. "Aryl" means an aromatic hydrocarbon radical provided by a homocyclic ring system, such as phenyl, and naphthyl. "Acyl" means a carbonyl radical attached to a hydrocarbon moiety, typically an alkyl or lower alkyl group.

Based upon the foregoing, the meanings of the following terms should be readily discernible, namely, "acylaminoalkyl", "cycloalkyl", "cycloalkylalkyl", "phenylalkyl" and "alkoxy".

In the cyclic structures of Formulae III, IV and V where the substituent T is shown, it is intended that the T substituent represents one or more substituents which may be attached at any substitutable position on any of the described cyclic structures.

Compounds of Formula I may have two or more carbon atoms providing asymmetric sites which are important for conferring activity. Preferred compounds have three asymmetric carbons which tend to confer improved activity. Such compounds whether in their pure isomer form or as components of racemic mixtures are embraced in the Formula I and II compounds of the invention. Many of the more active renin inhibitors are provided by compounds having a specific stereochemical configuration. Within Formula I, reading from the N terminus to the C terminus (terminating with the diol moiety), the preferred configurations for the asymmetric carbons are as follows: R,S,S,R,S.

Compounds of Formula I have been found to inhibit the production of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I.

These compounds can be formulated into pharmaceutically-acceptable dosage forms by any of a number of well-known carriers or diluents. The compounds can be formulated using pharmacologically-acceptable acid addition salts and can be used in a suitable hydrated form. The formulated compounds can be administered in oral dosage forms such as tablets, capsules, pills, powders, or granules. The compounds can also be administered intramuscularly, using forms known to the pharmaceutical art. In general, the preferred form of administration is oral. A therapeutically-effective but non-toxic quantity of the compound is employed in treatment of high blood pressure in mammals. The dosage regimen for preventing or treating hypertension with the compounds of Formula I is selected upon consideration of a variety of factors, including the type, age, weight, sex, and medical condition of the patient, the severity of the hypertension, the route of administration, and the particular compound employed. Dosages of the compounds are ordinarily in the range from about 0.5 to about 100 mg/kg (active compound-to-body weight), and preferably from about 1.0 to about 20 mg/kg given orally or by injection.

Compounds of Formula I are also useful as diagnostic agents for identification of hypertension due to renin excess.

Compounds of Formula I can be administered as prodrugs. Preferably, esterification of one or more of the hydroxyl groups of the compounds of Formula I is accomplished with amino acids to make aminoesters, succinates to make succinic acid esters, or phosphates to make phosphoric acid esters. Aminoesters of the Formula I compounds are more preferred.

Procedures for preparation of compounds of Formula I are set forth in the schemes and descriptions under Generic Synthesis I and Generic Synthesis II, taken with the specific procedures described in Examples 1–9 which follow thereafter. The substituents X and $R_1$ through $R_6$ are as described above for the Formula I substituents.

Generic Synthesis Outlines I & II

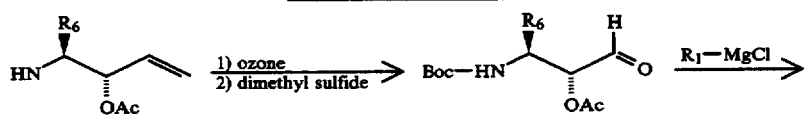

-continued

Generic Synthesis Outlines I & II

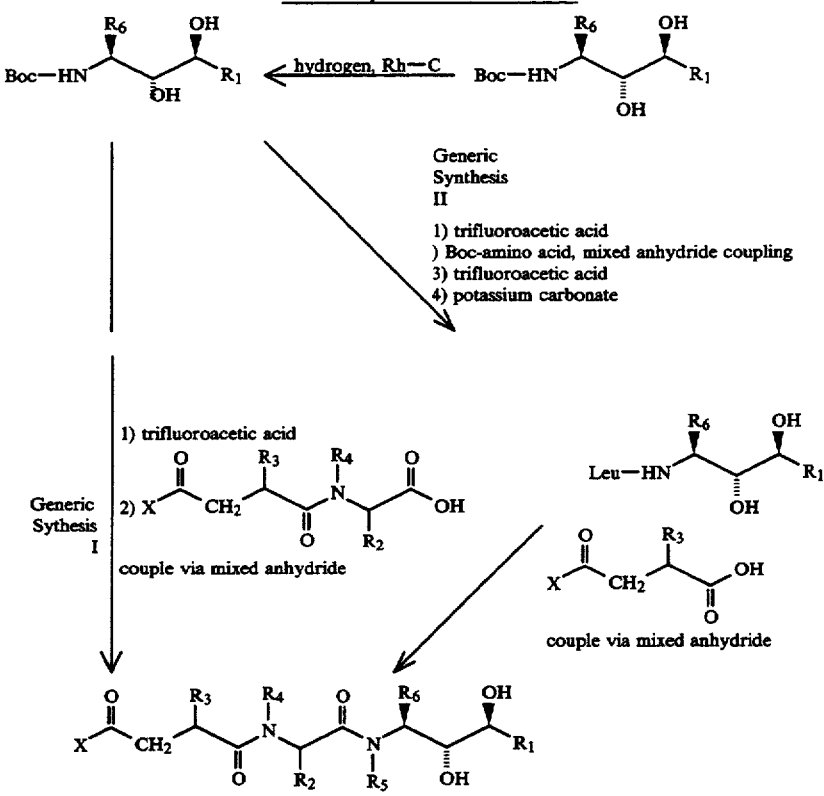

Generic Synthetic Description I

An allylic acetate, appropriately substituted and suitably protected, as shown in the scheme is used as starting material. This substance, and like substances, are ozonized under standard conditions (low temperature, as methanol-methylene chloride solutions) and the reduction of the ozonide to an aldehyde is effected with dimethyl sulfide. Once obtained, this type of aldehyde is treated with organometallic reagents capable of delivering an alkyl group to the aldehyde to produce diols of the type shown. These diols may then be converted, using standard peptide coupling methodology to renin inhibitors as shown via coupling to the general acid shown in the scheme. The initially obtained diol may also be hydrogenated to the saturated cyclohexane diol and again, coupled to in a similar manner to acids of the general description given in the scheme.

Generic Synthetic Description II

Diols are obtained as before, but using this method, stepwise coupling is carried out, using standard methodology developed for peptide synthesis, to obtain the renin inhibitors depicted in the scheme.

The following Synthetic Scheme is a more specific description of the preceeding Generic Synthesis Outlines I and II. This Synthetic Scheme outlines preparations of the specific compounds of Examples 1-9, which follow.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees Centigrade. Within the foregoing synthetic description and examples which follow, abbreviations have meanings as indicated below:

BOC=butyloxycarbonyl
i-Bu=isobutyl
Leu=leucine
Ac=acyl
Me=methyl
TFA=trifluoroacetic acid
THF=tetrahydrofuran

EXAMPLE 1

(3S,4S)-N-[(tert-Butyloxy)carbonyl]-4-amino-3-acetoxy-5-phenylpentene

The preparation of the above intermediate was carried out using the procedure described in Hanson, et al., (1985) J. Org. Chem. 50,5399.

EXAMPLE 2

(2R, 3S)-N-[(tert-Butyloxy)carbonyl]-3-amino-2-acetoxy-4-phenylbutanal

The preparation of the above intermediate was carried out as described in Hanson, et al. above. Ozone/oxygen was bubbled at −70° into a solution of 2.55 g (8.0 mmol) of the allylic acetate of Example 1 in 100 mL of methylene chloride until a deep blue color persisted. Oxygen was introduced until the blue color completely faded, then 3.0 mL of Me$_2$S was added and the solution was allowed to warm to 0°–5° and stand overnight. The solvent was removed at 0° under vacuum yielding the title compound as a thick yellow oil which was used in the following step without purification.

EXAMPLE 3

(2S, 3R, 4S)-N-[(tert-Butyloxy)carbonyl]-2-amino-1-phenyl-3,4-dihydroxy-6-methylheptane The oil prepared in Example 2 was dissolved under nitrogen in 100 mL of dry THF and cooled to −70°. To this solution was added 13 mL (26mmol) of a 2.0M solution of isobutylmagnesium chloride in ether and the stirred mixture was allowed to warm to room temperature and stir for 2 hrs. After decomposition with MeOH/H$_2$O the mixture was diluted with ether, washed with saturated NH$_4$Cl solution twice, then dried and the solvents stripped off under vacuum. The residue was allowed to stand overnight in 80% MeOH-H$_2$O containing in excess ammonium hydroxide. The MeOH was stripped off and the mixture was extracted with ether. These extracts were combined, washed with water, dilute KHSO$_4$,, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°–136°, Rf (ether): single spot, 0.6. By chromatography of the mother liquors and crystallization of the appropriate fractions, an additional 0.22 g of product, mp 138°–139° was obtained.

Anal: Calcd. for C$_{19}$H$_{31}$NO$_4$ (337.45): C, 67.62; H, 9.26; N, 4.15. Found: C, 67.51; H, 9.43; N, 4.24.

EXAMPLE 4

(2S,3R,4S)-N-[(tert-Butyloxy)carbonyl]-2-amino-1-cyclohexyl-3,4-dihydroxy-6-methylheptane The diol of Example 3, 0.27 g, was reduced in MeOH with 60 psi H$_2$ at 60° in 3 hrs using 5% Rh/C catalyst. After filtering, the solvent was stripped off and the 0.27 g of white crystals were recrystallized from CH$_2$Cl$_2$-hexane to furnish tiny needles of the title compound, 0.19 g, mp 126°–128°; further recrystallization gave mp 128.5°–129.5° Rf (ether): single spot, 0.8.

Anal: Calcd. for C$_{19}$H$_{37}$NO$_4$ (343.0): C, 66.43; H, 10.86, N, 4.08. Found: C, 66.43; H, 11.01; N, 4.03.

EXAMPLE 5

(2S,3R)-Boc-L-Leucinamide of 2-amino-1-cyclohexyl-3,4-dihydroxybutane

The procedure of Example 4 was employed using (2S,3R)-N-Boc-2-amino-1-phenyl-3,4-dihydroxybutane, prepared by the method of Hanson, et al. (1985) J. Org. Chem. 50, 5399–540, to give the crystalline 1-cyclohexyl derivative:

Anal. calcd for C$_{15}$H$_{29}$NO$_4$: C,62.69; H,10.17: N,4.87. Found: C62.69; H,10.51; N,4.91. This compound was treated with TFA and coupled to Boc-L-leucine using the coupling procedure in Example 9 to give the title compound.

EXAMPLE 6

D,L-Monomethyl-2-(1-naphthylmethyl)succinate

To a solution of diisopropylamine (36.6 g, 362mmol) in dry THF (200 ml) cooled to −78° for 30 minutes. To this solution was added monomethyl succinate (23.8 g, 180 mmol) in THF (200 mL) over a 30 minute period, and the reaction mixture was allowed to stir at −78° for 1 hour. To this mixture, 1-(bromomethyl)naphthylene (40 g, 191 mmol) in THF (220 mL) was added over a 30 minute period, and the solution was stirred for 1 hour at −78° then room temperature for 18 hours. The moisture was diluted with ether and extracted with water. The aqueous extracts were combined and acidified to pH 1 with 10% aqueous HCl, extracted with either and the organic extracts dried over sodium sulfate, filtered, and the solvent evaporated. The yellow solid residue was dissolved in hot toluene and hexane was added until the solution become cloudy. The solution was cooled, filtered and the title compound was isolated as a pale yellow solid (21 g).

Anal. calcd for C$_{16}$H$_{16}$O$_4$: C, 70.58; H, 5.92. Found: C, 69.03; H,5.99.

EXAMPLE 7

D,L-Methyl3-(N-morpholinocarbonyl)-2-(1-naphthylmethyl)propionate

The title compound of Example 6 (6 g, 22 mmol was dissolved in methylene chloride (50 mL) and the solution cooled to 0°. Thionyl chloride (10.5 g, 88 mmol) was added over a 2 minute period. The solution was then allowed to warm to room temperature and was stirred for 2 hours. Solvent and excess thionyl chloride were removed under vacuum and the residue was dissolved in methylene chloride. To this solution was added morpholine (5.75 g, 66 mmol) in methylene chloride (50 mL) over a 15 minute period. The mixture was stirred at room temperature for 18 hours, washed with 10% aqueous HCl followed by saturated aqueous potassium hydrogen carbonate, dried over sodium sulfate and chromatographed on silica gel eluting with 30/70 ethyl acetate-methylene chloride to obtain the title compound (4.48 g):

Anal. calcd: C$_{20}$H$_{23}$O$_4$: C, 71.20; H, 5.68; N, 4.15. Found: C,69.12: H,7.03; N,3.79.

EXAMPLE 8

D,L-3-(N-Morpholinocarbonyl)-2-(1-naphthylmethyl)-propionic acid

The title compound of Example 7 (4.38 g, 8 mmol) was dissolved in methanol (25 mL) and treated with aqueous sodium hydroxide (2N, 12.87 mL). The resulting solution was stirred for 6 hours at room temperature, then the solution was reduced to a small volume in vacuo and the residue was taken up in water. Concentrated aqueous HCl was added dropwise until pH 1 was reached, then the mixture was extracted with ethyl acetate. The organic extracts were dried over sodium sulfate and the solvent evaporated to obtain the title compound as a solid (4.15 g):

Anal. calcd for C$_{19}$H$_{21}$O$_4$: C,69.71: H,6.47; N,4.28. Found C,68.47; H,6.74; N,3.96.

EXAMPLE 9

3-(N-morpholinocarbonyl)-2-(R,S)-(1-naphthylmethyl)propionyl-L-leucinamide of (2S,3R)-2-amino-1-cyclohexyl-3,4-dihydroxybutane The title compound of Example 5 was treated with trifluoroacetic acid to remove the Boc group and this salt (96 mg) was dissolved in methylene chloride and treated with N-methylpiperidine (23 mg) to form Solution A. The title compound of Example 8 (109 mg) was dissolved in methylene chloride and treated with N-methylpiperidine (33 mg), then cooled to −10°. To this solution was added isobutylchloroformate (43 mg) and after 4 minutes, Solution A was added. This mixture was allowed to stir at −10° for hours and then the solvent was evaporated to give an oily residue. This was taken up in methanol and in potassium hydroxide was added; after 5 minutes, 0.5M citric acid was added and the mixture extracted with acetate. The organic layer was washed with 5% aqueous potassium carbonate, brine, and dried over sodium sulfate give the title compound as a white foam (97 mg): 400 MHz $^1$H NMR (CDCl$_3$): consistent with proposed structure:

Anal. calcd for $C_{35}H_{51}N_3O_6 + 0.75 H_2O$: C,67.44; H, 8.48; N, 6.74. Found: C, 67.37; H, 8.25; N, 6.42.

Biological Evaluation

Compounds of Formula i were evaluated as inhibitors of human renin in an in vitro assay, as follows: This human renin inhibition test has been previously described in detail [Papaioannou, et al., Clinical and Experimental Hypertension, A7(9), 1243–1257 (1985)]. Human renin was obtained from the National Institute for Biological Standards, London. In a total volume of 0.25 mL 100 mM Tris-acetate buffer at pH 7.4, 25×10-6 Goldblatt units of renin, 0.05 mL of plasma from human volunteers taking oral contraceptives, 6.0 mM sodium EDTA, 2.4 mM phenylmethyl sulfonyl fluoride, 1.5 mM 8-hydroxyquinoline, 0.4 mg/mL BSA, and 0.024 mg/mL neomycin sulfate were incubated for two hours at 37° C. in the presence or absence of renin inhibitors. The produced angiotensin I was determined by radioimmunoassay (New England Nuclear kit). Compounds to be assayed were solubilized in either ethyl alcohol or DMSO and diluted with 100mM Tris-acetate buffer at pH 7.4 to the appropriate concentration. The final concentration of organic solvent in the reaction mixture was less than 1%. Control incubations at 37° C. were used to correct for effects of organic solvent on renin activity.

The hog renin inhibition assay was performed in a manner similar to the human renin assay, with the following modifications. Hog renin was purchased from Sigma Chemical Co. and the synthetic tetradecapeptide substrate was obtained from Peninsula Labs Inc. In a final volume of 0.25 mL 100 mM Tris-acetate buffer at DH 7.4, 0.125 m units hog renin, 20 micromolar tetradecapeptide, 6 mM disodium EDTA, 3.2 mM phenylmethyl sulfonyl fluoride, 3 mM 8-hydroxyquinoline, 1.2 mg/mL BSA and 0.024 mg/mL neomycin sulfate were incubated for one hour at 37° C. in the presence or absence of renin inhibitors. The amount of angiotensin I produced was determined as for the human renin inhibition assay.

TABLE I

| Compound | Human Renin IC$_{50}$ | Hog Renin IC$_{50}$ |
|---|---|---|
| Example 9 | 7.4 × 10$^{-7}$M | 2.8 × 10$^{-6}$M |

Although this invention has been described with respect to specific embodiments, the details of these embodiments are not to be construed as limitations. Various equivalents, changes and modifications may be made without departing from :he spirit and scope of this invention, and it is understood that such equivalent embodiments are part of this invention.

What is claimed is:

1. A compound of the formula:

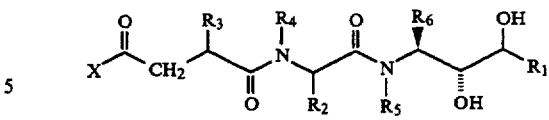

wherein X is

wherein T is selected from one or more groups selected from linear or branched lower alkyl, lower alkoxy, oxo, halo, haloloweralkyl, lower alkenyl, lower alkynyl and cyano; wherein R$_1$ is selected from linear or branched lower alkyl, haloloweralkyl, lower alkylcycloalkyl, lower alkylcycloalkenyl and lower alkoxycarbonyl; wherein R$_2$ is selected from linear or branched lower alkyl and benzyl; wherein R$_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein each of R$_4$ and R$_5$ is independently selected from H or lower alkyl; and wherein R$_6$ is selected from substituted or unsubstituted cycloalkyl, phenyl, cycloalkylalkyl and phenylalkyl, any one of which may be substituted with one or more groups selected from lower alkyl, lower alkoxy, halo, haloloweralkyl, lower alkenyl, lower alkynyl and cyano.

2. Compound of claim 1 of the Formula:

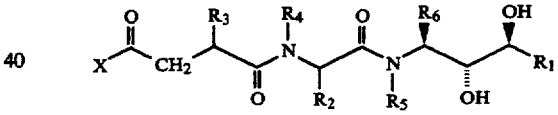

wherein X and R$_1$ through R$_6$ are as defined in claim 1.

3. Compound of claim 2 wherein T is selected from one or more groups selected from lower alkyl, lower alkoxy, oxo and halo; wherein R$_3$ is selected from lower alkyl, lower alkylcycloalkyl and lower alkoxycarbonyl; wherein R$_2$ is selected from lower alkyl and benzyl; wherein R$_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein R$_4$ is selected from H and lower alkyl; wherein R$_5$ is H or lower alkyl; and wherein R$_6$ is selected from cyclohexylmethyl and benzyl.

4. Compound of claim 3 wherein T is one or more of lower alkyl and lower alkoxy; wherein R$_1$ is H or lower alkyl; wherein R$_2$ is lower alkyl; wherein R$_3$ is benzyl; wherein R$_4$ is H or methyl; wherein R$_5$ is H or methyl; and wherein R$_6$ is cyclohexylmethyl.

5. A pharmaceutical composition comprising a therapeutically-effective amount of a renin-inhibiting compound and a pharmaceutically-effective carrier or diluent, said renin-inhibiting compound selected from a family of compounds of the formula:

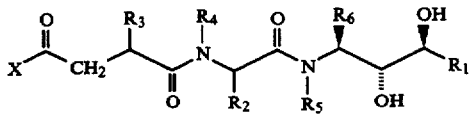

wherein X is

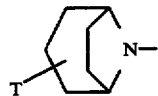

wherein T is selected from one or more groups selected from linear or branched lower alkyl, lower alkoxy, oxo, halo, haloloweralkyl, lower alkenyl, lower alkynyl and cyano; wherein $R_1$ is selected from linear or branched lower alkyl, haloloweralkyl, lower alkylcycloalkyl, lower alkylcycloalkenyl and lower alkoxycarbonyl; wherein $R_2$ is selected from linear or branched lower alkyl and benzyl; wherein $R_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein each of $R_4$ and $R_5$ is independently selected from H or lower alkyl; and wherein $R_6$ is selected from substituted or unsubstituted cycloalkyl, phenyl, cycloalkylalkyl and phenylalkyl, any one of which may be substituted with one or more groups selected from lower alkyl, lower alkoxy, halo, haloloweralkyl, lower alkenyl, lower alkynyl and cyano.

6. The composition of claim 5 wherein T is selected from one or more groups selected from lower alkyl, lower alkoxy, oxo and halo; wherein $R_1$ is selected from lower alkyl, lower alkylcycloalkyl and lower alkoxycarbonyl; wherein $R_2$ is selected from lower alkyl and benzyl; wherein $R_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein $R_4$ is selected from H and lower alkyl; wherein $R_5$ is H or lower alkyl; and wherein $R_6$ is selected from cyclohexylmethyl and benzyl.

7. The composition of claim 6 wherein T is one or more of lower alkyl and lower alkoxy; wherein $R_1$ is H or lower alkyl; wherein $R_2$ is lower alkyl; wherein $R_3$ is benzyl; wherein $R_4$ is H or methyl; wherein $R_5$ is H or methyl; and wherein $R_6$ is cyclohexylmethyl.

8. A therapeutic method for treating hypertension, said method comprising administering to a hypertensive patient a therapeutically-effective amount of a compound of the Formula:

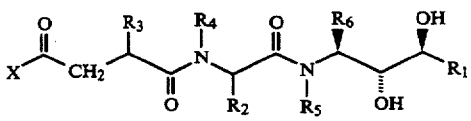

wherein X is

wherein T is selected from one or more groups selected from linear or branched lower alkyl, lower alkoxy, oxo, halo, haloloweralkyl, lower alkenyl, lower alkynyl and cyano; wherein $R_1$ is selected from linear or branched lower alkyl, haloloweralkyl, lower alkylcycloalkyl, lower alkylcycloalkenyl and lower alkoxycarbonyl; wherein $R_2$ is selected from linear or branched lower alkyl and benzyl; wherein $R_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein each of $R_4$ and $R_5$ is independently selected from H or lower alkyl; and wherein $R_6$ is selected from substituted or unsubstituted cycloalkyl, phenyl, cycloalkylalkyl and phenylalkyl, any one of which may be substituted with one or more groups selected from lower alkyl, lower alkoxy, halo, halo- loweralkyl, lower alkenyl, lower alkynyl and cyano.

9. The method of claim 8 wherein T is selected from one or more groups selected from lower alkyl, lower alkoxy, oxo and halo; wherein $R_1$ is selected from lower alkyl, lower alkylcycloalkyl and lower alkoxycarbonyl; wherein $R_2$ is selected from lower alkyl and benzyl; wherein $R_3$ is selected from lower alkyl, lower alkylcarbonylaminoalkyl, benzyl, naphthylmethyl, phenyl, naphthyl and benzyl substituted at the phenyl portion by halo or lower alkyl or by both; wherein $R_4$ is selected from H and lower alkyl; wherein $R_5$ is H or lower alkyl; and wherein $R_6$ is selected from cyclohexylmethyl and benzyl.

10. The method of claim 9 wherein T is one or more of lower alkyl and lower alkoxy; wherein $R_1$ is H or lower alkyl; wherein $R_2$ is lower alkyl; wherein $R_3$ is benzyl; wherein $R_4$ is H or methyl; wherein $R_5$ is H or methyl; and wherein $R_6$ is cyclohexylmethyl.

* * * * *